United States Patent
Sahl

(10) Patent No.: US 10,076,429 B2
(45) Date of Patent: Sep. 18, 2018

(54) MEMBRANE IMPLANT FOR TREATMENT OF CEREBRAL ARTERY ANEURYSMS

(75) Inventor: Harald Sahl, Wolfenbüttel (DE)

(73) Assignee: Phenox GmbH, Bochum (DE)

( * ) Notice: Subject to any disclaimer, the term of this patent is extended or adjusted under 35 U.S.C. 154(b) by 468 days.

(21) Appl. No.: 13/054,747

(22) PCT Filed: Jul. 15, 2009

(86) PCT No.: PCT/EP2009/005139
§ 371 (c)(1),
(2), (4) Date: Apr. 5, 2011

(87) PCT Pub. No.: WO2010/006777
PCT Pub. Date: Jan. 21, 2010

(65) Prior Publication Data
US 2011/0184451 A1    Jul. 28, 2011

(30) Foreign Application Priority Data

Jul. 17, 2008  (DE) .................... 20 2008 009 604 U

(51) Int. Cl.
| | |
|---|---|
| *A61M 29/00* | (2006.01) |
| *A61F 2/856* | (2013.01) |
| *A61B 17/12* | (2006.01) |
| *A61F 2/07* | (2013.01) |
| *A61F 2/92* | (2013.01) |
| *A61F 2/954* | (2013.01) |
| *A61F 2/966* | (2013.01) |
| *A61F 2/82* | (2013.01) |
| *A61F 2/30* | (2006.01) |

(52) U.S. Cl.
CPC ........ *A61F 2/856* (2013.01); *A61B 17/12022* (2013.01); *A61B 17/12118* (2013.01); *A61F 2/07* (2013.01); *A61F 2/92* (2013.01); *A61F 2/954* (2013.01); *A61F 2/966* (2013.01); *A61B 2017/1205* (2013.01); *A61F 2/82* (2013.01); *A61F 2002/3008* (2013.01); *A61F 2002/823* (2013.01); *A61F 2250/006* (2013.01); *A61F 2250/0098* (2013.01)

(58) Field of Classification Search
CPC .. A61F 2/856; A61F 2/07; A61F 2/966; A61F 2/954; A61F 2/92; A61F 2250/006; A61F 2002/823; A61F 2/82; A61F 2250/0098; A61F 2002/3008; A61B 17/12118; A61B 17/12022; A61B 2017/1205
USPC ........................ 606/200; 623/1.11–1.12, 1.23
See application file for complete search history.

(56) References Cited

U.S. PATENT DOCUMENTS

| | | | | |
|---|---|---|---|---|
| 5,061,275 A | * | 10/1991 | Wallsten et al. ............. | 623/1.22 |
| 5,211,658 A | * | 5/1993 | Clouse ........................ | 623/1.14 |
| 5,454,788 A | * | 10/1995 | Walker et al. ............. | 604/99.04 |

(Continued)

*Primary Examiner* — Amy R Weisberg
(74) *Attorney, Agent, or Firm* — Berliner & Associates

(57) ABSTRACT

The invention relates to a membrane implant (1) for treatment of cerebral artery aneurysms (10), wherein the implant can be implanted endovascularly into vessel segments (2) at the craniocerebral base of pathological (aneurysmatic) dilation (10) and, in combination with a stent, bridges the diseased vessel segment (2) from inside and disconnects it from the blood stream, wherein the membrane implant (1) comprises a biocompatible plastic membrane in the shape of a cylinder or a segment of a cylinder.

12 Claims, 3 Drawing Sheets

(56) References Cited

U.S. PATENT DOCUMENTS

| | | | |
|---|---|---|---|
| 5,682,894 A * | 11/1997 | Orr et al. | 600/431 |
| 5,713,948 A * | 2/1998 | Uflacker | A61F 2/07 |
| | | | 606/194 |
| 5,749,880 A * | 5/1998 | Banas | A61F 2/07 |
| | | | 606/198 |
| 5,749,894 A * | 5/1998 | Engelson | 606/213 |
| 5,769,882 A * | 6/1998 | Fogarty et al. | 128/898 |
| 5,928,279 A * | 7/1999 | Shannon et al. | 623/1.13 |
| 5,948,018 A * | 9/1999 | Dereume et al. | 623/1.12 |
| 5,951,599 A * | 9/1999 | McCrory | 606/108 |
| 6,093,199 A * | 7/2000 | Brown | A61B 17/12022 |
| | | | 606/200 |
| 6,330,884 B1 * | 12/2001 | Kim | 128/898 |
| 6,371,953 B1 * | 4/2002 | Beyar et al. | 623/1.1 |
| 6,461,370 B1 * | 10/2002 | Gray et al. | 606/200 |
| 6,530,939 B1 * | 3/2003 | Hopkins et al. | 606/200 |
| 6,537,310 B1 * | 3/2003 | Palmaz et al. | 623/1.13 |
| 6,616,679 B1 * | 9/2003 | Khosravi et al. | 606/200 |
| 6,656,214 B1 * | 12/2003 | Fogarty et al. | 623/1.13 |
| 6,726,703 B2 * | 4/2004 | Broome et al. | 606/200 |
| 6,786,920 B2 * | 9/2004 | Shannon et al. | 623/1.13 |
| 6,790,225 B1 * | 9/2004 | Shannon et al. | 623/1.13 |
| 6,802,851 B2 * | 10/2004 | Jones et al. | 606/200 |
| 7,713,282 B2 * | 5/2010 | Frazier et al. | 606/200 |
| 8,425,548 B2 * | 4/2013 | Connor | 606/194 |
| 8,470,013 B2 * | 6/2013 | Duggal et al. | 623/1.1 |
| 2001/0032009 A1 * | 10/2001 | Layne | A61F 2/07 |
| | | | 623/1.13 |
| 2004/0044361 A1 * | 3/2004 | Frazier et al. | 606/200 |
| 2004/0193246 A1 * | 9/2004 | Ferrera | 623/1.15 |
| 2005/0234501 A1 * | 10/2005 | Barone | 606/200 |
| 2005/0267570 A1 * | 12/2005 | Shadduck | 623/1.44 |
| 2006/0136043 A1 * | 6/2006 | Cully | A61B 17/0057 |
| | | | 623/1.22 |
| 2006/0184238 A1 * | 8/2006 | Kaufmann et al. | 623/1.53 |
| 2006/0206199 A1 * | 9/2006 | Churchwell et al. | 623/1.25 |
| 2007/0168018 A1 * | 7/2007 | Amplatz et al. | 623/1.18 |
| 2007/0191884 A1 * | 8/2007 | Eskridge | A61B 17/12022 |
| | | | 606/213 |
| 2008/0319521 A1 * | 12/2008 | Norris et al. | 623/1.5 |
| 2010/0152834 A1 | 6/2010 | Hannes et al. | |
| 2011/0224707 A1 | 9/2011 | Miloslavski et al. | |
| 2013/0138198 A1 | 5/2013 | Aporta et al. | |
| 2013/0211492 A1 | 8/2013 | Schneider et al. | |
| 2013/0296916 A1 | 11/2013 | Monstadt et al. | |
| 2014/0058420 A1 | 2/2014 | Hannes et al. | |
| 2014/0058498 A1 | 2/2014 | Hannes et al. | |
| 2014/0343595 A1 | 11/2014 | Monstadt et al. | |

* cited by examiner

MEMBRANE IMPLANT FOR TREATMENT OF CEREBRAL ARTERY ANEURYSMS

The invention relates to a membrane implant for treatment of cerebral artery aneurysms, wherein the implant can be implanted endovascularly into vessel segments at the craniocerebral base of pathological (aneurysmatic) dilation and, in combination with a stent, bridges the diseased vessel segment from inside and disconnects it from the blood stream.

A radiological-interventional treatment of the described pathological dilation of arteries (aneurysms) by means of endovascular (i.e. passing through the blood stream) implantation of covered metal grate prostheses (stents) impermeable to blood applied outside the cranium constitutes common and successful practice. A diseased vessel segment is thus bridged, thereby preventing further growth and ultimately a rupture of the aneurysm.

When applied to vessels of the craniocebral base, this concept has hitherto usually failed because available covered stents or their introducer kits are not flexible enough to be able to push them forward into diseased vessel segments. Up to now, only non-covered stents are available which feature sufficient flexibility in terms of the introducer kits, too. However, owing to their permeability to blood, such stents cannot disconnect the aneurysms from blood circulation.

Hence the problem underlying the present invention is to create an endovascularly placeable implant which in combination with already available non-covered stents is capable of assuming the function of a hitherto (and predictably) non-available suitable covered stent to treat cerebral artery aneurysms.

This problem is solved with a membrane implant of the nature described hereinabove that is comprised of a biocompatible plastic membrane in the shape of a cylinder or a cylinder segment.

By way of the present invention it is achieved that a diseased vessel segment with the aneurysm is bridged from inside with a membrane and disconnected from the blood stream. The membrane implant is folded-up and moved in a microcatheter forward into the diseased vessel segment. Upon correct placement, the implant is unfolded by retracting the microcatheter and definitively fixed and stabilized by the aid of a stent so that the functionality of a covered stent is achieved. The drawback of insufficient flexibility is evaded by successive implantation of two flexible modules.

The inventive membrane implants as a rule have a length of 5 mm and 30 mm as well as a radius ranging between 1 mm and 3 mm, with these dimensions resulting from the dimension of the diseased vessel segment on the one hand and from the nature of vessel dilation on the other hand. The foils have a thickness in a range from 10 to 50 µm; they are comprised of a medically compatible plastic material, for example of polyurethane, polyalkylene, polyamide, polytetrafluoroethylene or PET.

The plastic membrane of the inventive implant is configured in the shape of a cylinder or cylinder segment, this shape resulting from the expanded state in the vessel upon implantation. During implantation, the implant is guided in a microcatheter in a more or less folded-up condition. The cylinder or cylinder segment may be closed, but also open, i.e. slotted. The latter configuration bears the advantage that the membrane when placed in the vessel to be treated can adapt itself optimally to the vessel diameter, with it being possible for the side edges of the elongated slot to overlap each other slightly or to leave some clearance in longitudinal direction.

To achieve optimal adaptability to the vessel, and to maintain the implant under tension when implanted, it may be sensible to provide a self-erecting clasp at the proximal and/or distal end, said clasp fixing the cylinder shape and supporting it towards the vessel wall. Such a clasp may be made of a material having shape-memory properties, e.g. nitinol. For example, the clasp may also be made of a radiopaque material, such as platinum or a platinum alloy, or a material having shape-memory properties, such as nitinol which is provided with a radiopaque sheath. Such a sheath, for example, may be provided in form of a wire helix made of a radiopaque material like platinum or a platinum alloy.

Instead of wire clasps, it is also possible to provide plastic clasps that feature the demanded shape-memory properties.

The self-erecting clasps made of wire or plastic may border the cylinder of the plastic membrane at one end or at both ends completely or partly. A partial bordering is usually sufficient. Preference is given to bordering the membrane cylinder at the proximal end, i.e. at the end facing the guiding wire and/or blood stream.

Additionally or alternatively to a radiopaque self-erecting clasp, an X-ray visible flexible elongated wire may be provided which extends along the cylinder wall over the entire cylinder length and which is connected, if required, at one end or both ends with the self-erecting clasp. A wire made of platinum or a platinum alloy may serve as preferential material for this purpose. Alloys of platinum and iridium, in particular, have become known for X-ray visible implants.

Expediently, the inventive membrane implant is detachably connected to a guiding wire so that it can be reliably placed by the attending physician. For example, this connection can be established via a coupling point wherein the coupling elements are provided for at the guiding wire and at the proximal or distal clasp. If the clasp is made of a metal, spot welded joints are eligible which can be dissolved under the influence of electricity in an actually known manner. The technique is the same as the one developed for the placement of occlusion spirals in aneurysms.

In accordance with a preferred embodiment, the membrane implant is comprised of two membrane foils which are laid over each other. Each of the membrane foils may have a thickness of approx. 10 µm, for example. Clasps, wires or other elements, if any, may be arranged between the two membrane foils, with a fixation by welding-in or by an adhesive bond being eligible.

In the embodiment with two membrane foils, reinforcing filaments inserted between the foils may be provided, for example filaments made of nitinol which feature shape-memory properties. Such wires may be arranged at regular distances, for example at distances ranging from 1 to 10 mm, wherein these distances depend on the required tension force, the strength of the reinforcing filaments and the size of the implant. Preferably these wires extend obliquely, for example at an angle of 30 to 60° and in particular at an angle of approx. 55° versus the longitudinal direction of the implant, with it also being possible to provide for a crosswise arrangement of the wires, thus creating a network or latticework. For example, radiopaque filaments which allow for a pictorial representation of the implant in the body may also be worked-in into the threads having shape-memory properties.

As a matter of fact, the reinforcing filaments having shape-memory properties may also be made of a suitable plastic material.

As has been addressed hereinabove, the inventive implant is coupled to a guiding wire and can be released from it. Guiding wires of this type and nature are actually known in prior art. For example, they have a diameter of 0.014 inch (0.356 mm) and allow guiding the implant through a conventional microcatheter. It is expedient to guide such a guiding wire through the lumen of the cylindrically shaped implant and to make it radiopaque at its distal end. At its distal end or near the distal end, the guiding wire may be comprised of a plastic cone which is helpful on its guidance in the microcatheter and its placement at the diseased vessel segment.

In particular, the membrane implant may be comprised of a complete cylinder, but frequently it is also formed by a cylinder segment which is open at the side opposite to a side wall aneurysm so that vessels departing there are not occluded. In this case, the implant has the shape of an obliquely indented cylinder.

The invention finally relates to a kit comprised of an inventive membrane implant together with a dimensionally adapted stent as well as the guiding wires and catheters, if any, required to guide the stent and implant. As a rule, it is a stent crimped over a balloon and implanted by hydraulic expansion. In practice, it is also possible to utilize a stent which is made of a material having shape-memory properties, such as nitinol, and which when released from a microcatheter expands itself in situ and braces against the vessel wall under fixation of the membrane. Stents of this type and nature are actually known in prior art.

The invention is hereinafter explained in more detail by the enclosed drawings, where FIG. 1 shows a microcatheter with a folded-up implant (guided therein);

FIGS. 1 to 3 illustrate a practical example of the present invention for the treatment of so-called side wall aneurysms.

FIG. 4 shows a released, unfolded implant after detachment of the guiding wire in the way in which it can be utilized to treat spindle-shaped (fusiform) aneurysms.

Figure 5:
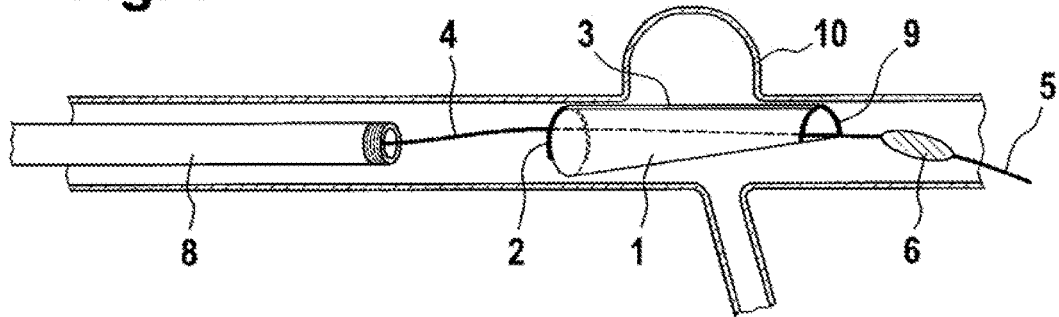
FIG. 5 shows a released, unfolded implant having the shape of a cylinder segment.

An embodiment of the invention for treatment of side wall aneurysms, opposite to which a vessel departs, and whose departure must not be occluded, is illustrated in FIG. 5. The implant is comprised of an obliquely indented membrane which proximally (facing the microcatheter and/or the attending physician) has the full circumference and which is distally (the side averted from the attending physician) shortened to a partial circumference. The departing vessel remains free on the open side of the membrane implant 1.

Depicted in the figures within the diseased vessel segment 10 is:
the membrane implant with membrane 1,
a proximal self-erecting radiopaque wire clasp for unfolding and primary fixation of membrane 2,
a flexible X-ray visible elongated wire to stabilize and mark the implant position 3,
a detachable guiding wire 4 with a flexible X-ray visible tip 5 and a plastic cone 6 at the exit from the microcatheter, the point of detachment of the guiding wire 7,
as well as a microcatheter with an X-ray visibly marked tip for forward movement 8.

For treatment of side wall aneurysms, opposite to which a vessel departs whose departure must not be occluded, as well as for treatment of spindle-shaped (fusiform) aneurysms, the membrane implant is additionally provided with an X-ray visible, self-erecting distal wire clasp 9 for the purpose of distal stabilization.

Figure 2:
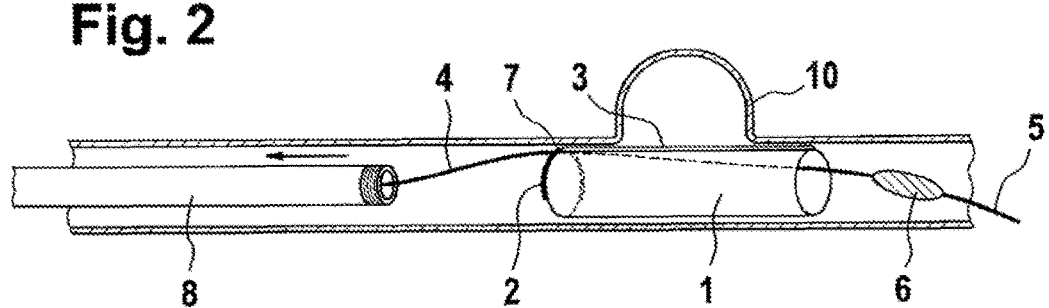
FIG. 2 shows the released, unfolded implant according to FIG. 1 prior to detachment of the guiding wire.

Upon retraction of the microcatheter which is required for forward movement to the site of implantation, the membrane supported by the self-erecting wire clasp(s) and the blood stream can unfold in the diseased vessel segment FIG. 2). While observing the X-ray visible elongated wire, in particular, an optimized placement with regard to longitudinal position and rotation of the membrane can be achieved. Upon subsequent detachment of the guiding wire (FIG. 3), the implant which is now only unstably fixed by the blood pressure and the wire clasp(s) is finally fixed in its position by way of a stent (introduced via the guiding wire already prior to the detachment) which must protrude the membrane implant proximally and distally.

Figure 1:
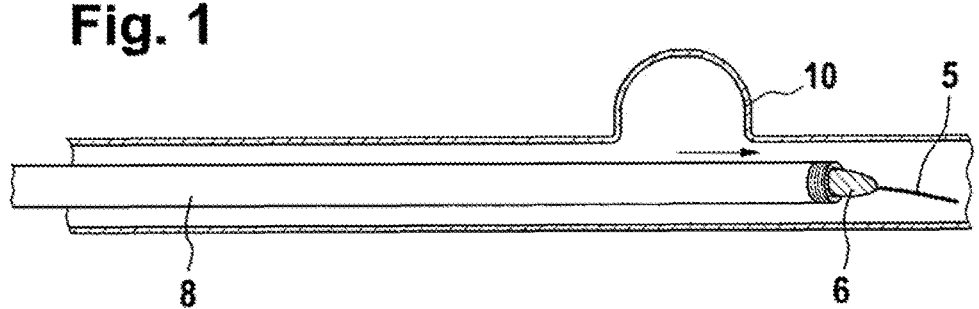
Figure 3:
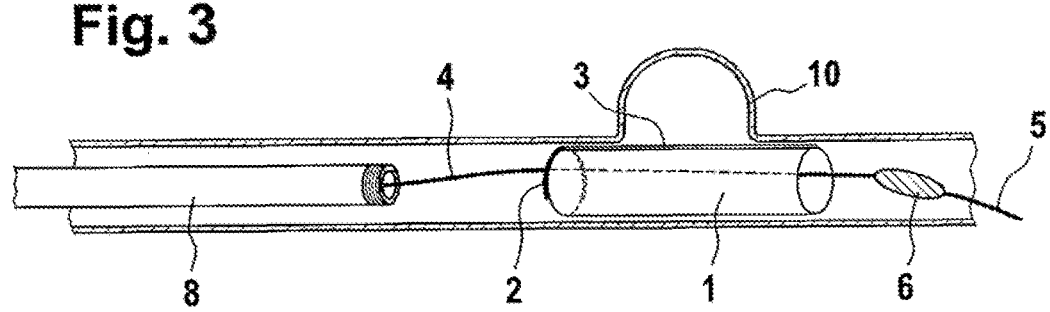
FIG. 3 shows the released, unfolded implant according to FIG. 1 after detachment of the guiding wire.

FIGS. 1 to 3 show a first embodiment of an inventive membrane implant in a blood vessel with a side wall aneurysm 10. Implant 1 has mainly cylindrical shapes and may be comprised of a tubular plastic cylinder, but as a rule it is formed by a plastic membrane sheet re-shaped to a cylinder. Located at the proximal end of membrane 1 is a metal clasp 2 which is preferably made of nitinol and which for the sake of better visibility may be sheathed with a radiopaque material. Extending in longitudinal direction is a flexible X-ray visible elongated wire 3 which enables the attending physician to place the implant exactly in relation to the side wall aneurysm 10.

The implant is brought via a microcatheter 8 which as a rule is comprised of a radiopaque tip to the site of treatment and released from it by the aid of a guiding wire 4. Guiding wire 4 is connected via a welding/detaching point 7 to the clasp 2 and can be detached electrolytically by a short impact of direct current (see FIG. 3). The guiding wire itself is comprised of an X-ray visible tip 5 together with a plastic ball or cone 6 which serves for navigation and imaging.

Figure 4:
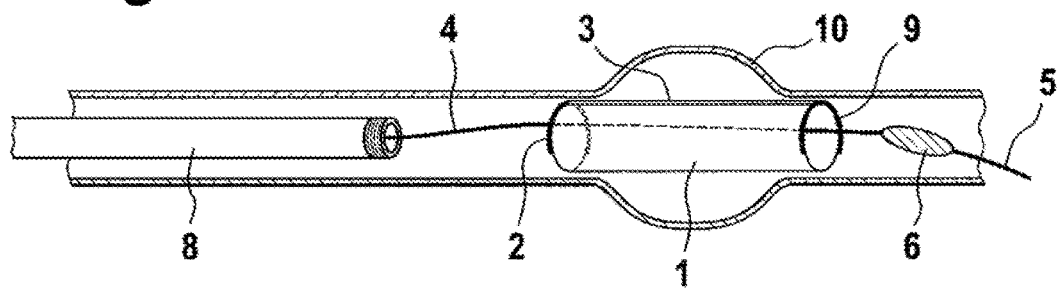
FIG. 4 shows the released, unfolded implant on treatment of fusiform aneurysms.

The plastic membrane is comprised of the self-erecting clasp 2, preferably at the proximal end, in order to lean the membrane to the vessel wall. A second clasp may be arranged distally, as depicted in FIG. 4. As a rule, it is sufficient to provide a proximal clasp which is located at the membrane implant side facing the blood stream. For fusiform aneurysms or malformations in which it matters to ensure good channelling of the blood stream past the malformation, however, it is expedient to provide a second clasp 9 also at the distal end of the membrane implant 1, see FIG. 4.

FIG. 5 illustrates the special case of a vascular malformation opposite to a vessel departure. In this case, the membrane implant must keep the departure clear which is why it is obliquely indented. In this case, too, self-erecting clasps 2 and 9 are located at the proximal and distal end of the membrane implant.

Figure 6A:
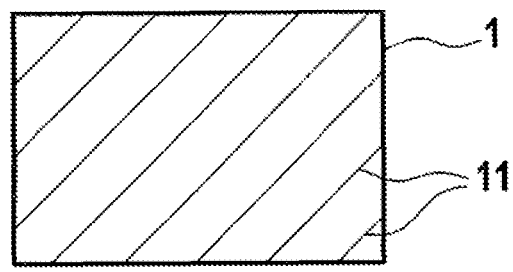
FIG. 6 shows an implant comprised of two plastic membranes and having nitinol filament inlays.
Figure 6B:
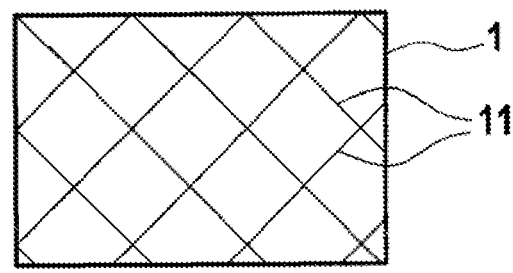

FIG. 6 shows a special configuration of a membrane implant which is comprised of nitinol filaments 11 laid-in to generate higher voltage. In this case, the implant is comprised of a double membrane with nitinol filament inlays which extend at a regular distance of 3 mm, for example, at an angle of 45° to the longitudinal direction of the implant (FIG. 6a). The reinforcing filaments may also build-up a latticework in which the reinforcing filaments 11 extend crisscross at right angles to each other, and also at an angle of 45° to the longitudinal direction of the implant (FIG. 6b). The implant is provided with a pre-tensioning in an actually known manner, pushed forward in rolled-up state and released in the same manner as shown, for example, in FIGS. 1 to 5. Accordingly, the guiding wire may be welded on to one of the reinforcing wires 1 and detached electrolytically in the well known manner. On its release from the microcatheter, the implant springs-up like a helical spring and leans itself to the vessel wall, thus occluding a malformation, e.g. a side wall aneurysm.

The nitinol filaments may be welded-in or bonded-in with an adhesive in the implant between the two covering foils. It is feasible to draw-in individual marker filaments made of a radiopaque material in order to make the membrane implant X-ray visible in this manner.

The inventive membrane implant is generally fixed and secured additionally at the implantation site by a subsequently introduced neurostent. Such a securing device, however, may be dispensable with the embodiment depicted in FIG. 6, because here the reinforcing filaments with a cylindrical shape impressed onto them (material having shape-memory properties) take charge of securing it in the vessel.

The invention claimed is:

1. A kit for treatment of a cerebral artery aneurysm, comprising
    a membrane implant comprising a biocompatible plastic membrane and a proximal self-erecting wire clasp connected to the membrane and designed for unfolding and primary fixation of the membrane inside a vessel against a vessel wall, the membrane configured to be outside of and bridging the aneurysm, wherein the biocompatible plastic membrane when expanded comprises an open cylinder segment shape having a lumen,
    a guiding wire extending through said lumen and ending distally from the membrane implant in a distal tip,
    said wire clasp being connected via a detaching point to the guiding wire, the detaching point being located proximally from said distal tip,
    a separate stent for fixation of the membrane implant against the vessel wall at the site of the aneurysm, thereby bridging the aneurysm, and
    an X-ray visible flexible elongated wire configured to extend longitudinally along the biocompatible membrane,
    and wherein the membrane implant and the separate stent together are configured to function as a covered stent.

2. The kit according to claim 1, characterized in that the membrane implant is between 5 mm and 30 mm long corresponding to the length of a vessel segment to be treated and has a radius corresponding to the radius of the vessel segment to be treated, ranging between 1 mm and 3 mm.

3. The kit according to claim 1, characterized in that the wire clasp is a self-erecting X-ray visible wire clasp.

4. The kit according to claim 1, characterized in that the guiding wire comprises a plastic cone at the transition to the wire's tip.

5. The kit according to claim 4, characterized in that the guiding wire comprises a flexible radiopaque tip.

6. The kit according to claim 1, characterized in that the biocompatible membrane is longitudinally slotted.

7. The kit according to claim 1, characterized in that the membrane implant is comprised of two membrane foils.

8. The kit according to claim 7, characterized by reinforcing filaments inserted between the two membrane foils.

9. The kit according to claim 8, characterized in that the reinforcing filaments are made of nitinol.

10. The kit according to claim 8, characterized in that the distance between the reinforcing filaments ranges between 1 and 10 mm.

11. The kit according to claim 8, characterized in that the reinforcing filaments extend obliquely at an angle of 30 to 60° to the longitudinal direction of the implant and that said filaments are possibly laid in crisscross arrangement.

12. The kit according to claim 7, characterized by one or more reinforcing filaments in the form of X-ray visible flexible wires.

* * * * *